United States Patent [19]

Wu

[11] 4,391,998

[45] Jul. 5, 1983

[54] PRODUCTION OF PARA-ISOPROPYLPHENOL

[75] Inventor: Margaret M. Wu, Belle Mead, N.J.

[73] Assignee: Mobil Oil Corporation, New York, N.Y.

[21] Appl. No.: 313,425

[22] Filed: Oct. 21, 1981

[51] Int. Cl.$^3$ ............................ C07C 37/14; C07C 39/06
[52] U.S. Cl. .................................... 568/781; 568/789; 568/790; 568/794; 252/455 Z; 568/784; 568/804
[58] Field of Search ............... 578/781, 789, 794, 790, 578/785, 784, 804; 252/455 Z

[56] References Cited

U.S. PATENT DOCUMENTS

| | | | |
|---|---|---|---|
| 2,684,389 | 7/1954 | Offutt | 568/791 |
| 3,071,595 | 1/1963 | Vesely et al. | 568/794 |
| 3,082,258 | 3/1963 | McConnell et al. | 568/792 |
| 3,133,974 | 5/1964 | Curry et al. | 568/789 |
| 3,185,737 | 5/1965 | Geddes, Jr. | 568/789 |
| 3,367,981 | 2/1968 | Napolitano | 568/781 |
| 3,426,358 | 2/1969 | Schliching et al. | 568/789 |
| 3,449,444 | 6/1969 | Habibi | 568/794 |
| 3,702,886 | 11/1972 | Argauer et al. | 568/328 |
| 3,728,408 | 4/1973 | Tobias | 568/790 |
| 3,959,394 | 5/1976 | Tasaka et al. | 568/781 |
| 3,992,455 | 11/1976 | Leston | 568/781 |
| 4,230,894 | 10/1980 | Young | 568/768 |
| 4,283,573 | 8/1981 | Young | 568/789 |

FOREIGN PATENT DOCUMENTS

| | | | |
|---|---|---|---|
| 871105 | 4/1979 | Belgium . | |
| 54-073738 | 6/1979 | Japan | 568/794 |

OTHER PUBLICATIONS

Venuto et al., "Journal of Catalysts", vol. 4, 81–98, (1966).
Friedel–Crafts and Related Reactions, Edited by G. A. Olah, vol. II, pp. 77–79, (Interscience, 1963).

Primary Examiner—Werren B. Lone
Attorney, Agent, or Firm—Charles A. Huggett; Michael G. Gilman; George W. Allen

[57] ABSTRACT

Phenol is catalytically alkylated with an isopropanol or propylene alkylating agent to form high yields of an isopropylphenol product enriched in the para-isomer of isopropylphenol. Such an alkylation process is carried out under catalytic alkylation conditions including a temperature of from about 200° C. to 300° C. and contact with a crystalline zeolite catalyst having a silica to alumina molar ratio of at least about 12 and a constraint index of about 1 to 12.

9 Claims, No Drawings

PRODUCTION OF PARA-ISOPROPYLPHENOL

BACKGROUND OF THE INVENTION

1. Field of the Invention

The present invention relates to the selective catalytic alkylation, e.g., propylation, of phenolic compounds to produce an alkylphenolic reaction product enriched in the para-isopropyl isomer of the phenol being alkylated.

2. Description of the Prior Art

Propylated phenolic compounds such as para-isopropylphenol are useful materials in the synthesis of various products such as adhesives, agricultural chemicals and pharmaceuticals. It is known to prepare such compounds via the alkylation of phenolic compounds with such propylating agents as propylene and isopropanol, and a variety of alkylation catalysts are known to promote such a reaction. For example, U.S. Pat. No. 3,959,394; 3,439,048; 3,426,358; 3,426,082; 3,409,678; 3,382,283; 3,367,981; 3,265,742; 3,185,737; 3,133,974; 3,082,258 and 3,071,595, all disclose alkylation of phenol over a variety of catalysts such as Friedel Crafts catalysts ($AlCl_3$, HF, $BF_3$, etc.), zinc halides, alumina, aluminum phenoxide, alkane sulfonic acids and the like. Although many of these reactions are said to favor formation of the ortho-alkylphenols, reaction products in all instances contain at least some of the para- and meta-isomers as well.

Separation of the para-isomer of propylated phenol from mixtures containing the other isomers of this compound is not economically attractive unless the product mixture contains a relatively high concentration of the para-isomer. Accordingly, attempts have been made to alkylate phenol under conditions which selectively promote formation of the para-alkylphenol isomer. Thus, for example, Belgian Pat. No. 871,105 discloses the para-selective alkylation of phenol with olefins over strongly acid ion exchange resin catalysts, and Japanese Patent Specification 54073738 discloses alkylation of phenol with olefins over titanium and molybdenum oxides followed by isomerization to the p-isomer over $H_2SO_4$ or silica-alumina.

Notwithstanding such efforts to maximize production of the para-isopropyl isomer during alkylation of phenol, there is a continuing need to identify additional phenol alkylation process procedures, conditions and catalysts which can be used to para-selectively synthesize desirable isopropylphenolic compounds. Accordingly, it is an object of the present invention to provide a process for alkylating phenol to produce a product mixture enriched in the para-isomer of isopropylated phenolic materials.

SUMMARY OF THE INVENTION

In accordance with the present invention, product mixtures containing especially high concentrations of the para-isomer of isopropylated phenolic compounds are formed by alkylating phenol with either isopropanol or propylene. Such an alkylation reaction is carried out by contacting phenol and alkylating agent in the presence of a crystalline zeolite catalyst having a silica to alumina molar ratio of at least about 12 and a constraint index within the approximate range of 1 to 12. Alkylation is conducted under alkylation conditions which include a temperature of from about 200°–300° C.

DETAILED DESCRIPTION OF THE INVENTION

Phenol is selectively alkylated in accordance with the process of the present invention. Alkylation is carried out by contacting phenol with alkylating agent, and the particular alkylating agent used in the process of the present invention is one which provides the para-isopropyl isomer of the phenol being alkylated. Thus, the alkylating agent used herein is selected from isopropanol and propylene and is employed in a molar ratio of phenol to alkylating agent of from about 0.5:1 to 20:1, preferably from about 1:1 to 5:1. The isopropanol or propylene alkylating agent may be utilized as a pure compound or may be admixed with one or more inert diluents as hereinafter more fully described.

Alkylation to produce isopropyl phenolic compounds is conducted in the present process in the presence of a particular type of para-selective crystalline zeolite catalyst. Such crystalline zeolites are members of a special class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 and preferably at least 30 are useful, it is also preferred in some instances to use zeolites having substantially higher silica/alumina ratios, e.g., 1600 and above. In addition, zeolites as otherwise characterized herein but which are substantially free of aluminum, that is, zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity), but which otherwise embody the characteristics disclosed.

Members of this particular class of zeolites, after activation, acquire an intracrystalline sorption capacity for normal hexane which is greater than that for water, i.e., they exhibit "hydrophobic" properties. This hydrophobic character can be used to advantage in some applications.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "Constraint Index" is calculated as follows:

Constraint Index =

$$\frac{\log_{10} (\text{fraction of hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Beta | 0.6 |
| ZSM-4 | 0.5 |
| H—Zeolon (mordenite) | 0.4 |
| REY | 0.4 |
| Amorphous Silica—Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the special class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, ZSM-48 and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

ZSM-48 is more particularly described in published European Patent Application No. 80 300,463, the entire content of which is incorporated herein by reference.

It is to be understood that by incorporating by reference the foregoing patents and application to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents and application should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites include ZSM-5, ZSM-11, ZSM-23, ZSM-35, ZSM-38, and ZSM-48, with ZSM-5, ZSM-11 and ZSM-23 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired.

Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968.

When the crystal structure is unknown, the crystal framework density may be determined by classical pyknometer techniques. For example, it may be determined by immersing the dry hydrogen forms of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the described alkylation process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The crystalline zeolites employed may be modified with respect to activity and/or selectivity prior to use by combining therewith a small amount, generally in the range of about 0.5 to about 40 weight percent, preferably of a difficulty reducible oxide, such as the oxides of phosphorous or magnesium or combinations thereof. Modification of the zeolite with the desired oxide or oxides can readily be effected by contacting the zeolite with a solution of an appropriate compound of the element to be introduced, followed by drying and calcining to convert the compound to its oxide form. It is also possible to modify the activity or selectivity of such zeolites by conventional steaming or precoking techniques.

In accordance with the present invention, the zeolite catalyst materials as hereinbefore described promote surprisingly para-selective alkylation of phenol when phenol is alkylated with either propylene or isopropanol. By using such zeolites as the alkylation catalyst, a reaction product enriched in the para-isomer of the isopropyl phenolic compound can be produced. Under the particular alkylation conditions of the present process, the isopropylphenol reaction product, in fact, frequently contains a major portion of the para-isopropyl isomer. Para-isomer concentration in such a reaction product is thus significantly above the equilibrium concentration of para-isomer in mixtures of this type. Para-isopropyl isomer concentration in the reaction product mixture is also significantly greater than that which results from propylation using conventional Friedel Crafts phenol alkylation catalysts such as boron trifluoride.

Furthermore, the alkylation process of the present invention is especially advantageous with respect to total isopropyl isomer production relative to the production of the n-propyl isomer or diisopropyl products. The yield of isopropylphenol is generally at least 45% of the total reaction product and can be as high as at least 60%.

Such selective alkylation is accomplished by contacting the phenol reactant with the propylene or isopropanol alkylating agent in the presence of the zeolite catalyst under alkylation conditions. Alkylation conditions for the process herein essentially include a temperature between about 200° C. and 300° C., preferably from about 250° C. and 300° C. It has been discovered that at temperatures in excess of 300° C., selectivity of the reaction to the para-isomer of the phenolic compound drops off.

Other reaction conditions employed in the process herein are those which are conventional for alkylation of aromatic compounds such as phenolics. The reaction generally takes place at atmospheric pressure, but the pressure may be within the approximate range of $10^5$ $N/m^2$ to $6 \times 10^6$ $N/m^2$ (1 atm to 60 atm). The reaction may be suitably accomplished utilizing a feed weight hourly space velocity (WHSV) of between about 0.5 and about 100, preferably between about 1 and about 40.

In addition to the phenol and propylene or isopropanol reactants, the reaction mixture may optionally contain various inert diluents to facilitate practice of the process. Common inert diluents can include water, air, nitrogen, carbon dioxide, lower alkanes and the like. Such diluents can comprise from about 0 up to about 50% by weight of the alkylation reaction mixture.

The process of this invention may be conducted with the organic reactants in either the gaseous or the liquid phase or both. It may be carried out as a batch-type, semi-continuous or continuous operation utilizing a fixed, fluidized or moving bed catalyst system.

The following examples will serve to illustrate the process of this invention but are not limiting thereof:

EXAMPLE I

Phenol is alkylated with an isopropanol alkylating agent over an amorphous aluminosilicate cracking catalyst. A 1:1 molar ratio mixture of phenol and isopropanol was passed through a four gram bed of the amorphous aluminosilicate material having an $SiO_2/Al_2O_3$ ratio of 90:10. The WHSV was maintained at 1 for a period of five hours while reaction temperature was varied between 250° C. and 400° C.

Alkylation results using this catalyst are summarized in TABLE I.

TABLE I

| Alkylation of Phenol with Isopropanol to Produce Isopropylphenol (IPP) Over Amorphous Aluminosilicate Catalyst | | | | | |
|---|---|---|---|---|---|
| Time on Stream (hours) | 1 | 2 | 3 | 4 | 5 |
| Temperature (°C.) | 250 | 300 | 350 | 400 | 300 |
| Conversion of Phenol (wt. %) | 36.6 | 27.4 | 18.2 | 8.6 | 14.5 |
| Selectivity (Area %) | | | | | |
| o - IPP | 21.85 | 18.64 | 12.51 | 6.77 | 26.74 |
| m - IPP | 41.47 | 31.95 | 10.99 | 7.24 | 44.55 |
| p - IPP | 20.36 | 12.67 | 4.92 | — | 19.91 |
| N—Propylphenols | 18.12 | 17.30 | 18.56 | 5.33 | 6.74 |
| Methyl & Ethyl Phenols | 8.64 | 17.44 | 51.84 | 80.68 | 2.05 |
| Others | 0 | 0 | 0 | 0 | 0 |
| Total Selectivity to IPPs | 62.02 | 46.38 | 19.59 | 9.79 | 68.47 |
| In IPP Fraction | | | | | |
| % Ortho | 26.11 | 29.47 | 44.02 | 48.32 | 29.32 |
| % Meta | 49.56 | 50.50 | 38.67 | 51.68 | 48.85 |
| % Para | 24.33 | 20.03 | 17.31 | 0 | 21.83 |

The TABLE 1 data indicate that phenol alkylation with isopropanol over amorphous aluminosilicate provides an isopropylphenol product which approaches equilibrium with respect to isomeric distribution. No selectivity toward para-isopropylphenol is provided. Furthermore, significant amounts of non-isopropylphenol reaction products are produced at all temperatures tested.

EXAMPLE II

The same phenol isopropanol feed of EXAMPLE I was contacted under essentially identical reaction conditions with an HZSM-5 zeolite catalyst of the type employed in the present invention. The HZSM-5 zeolite used had a $SiO_2/Al_2O_3$ molar ratio of about 70 and a crystal size of about 1 micron. The zeolite was combined with about 35 weight percent of an alumina binder. The catalyst composite is calcined at 500° C. in air before being used initially as an alkylation catalyst.

Results of alkylation at various temperatures and times on stream are set forth in TABLE II.

TABLE II

Alkylation of Phenol with Isopropanol to Produce Isopropylphenol (IPP) Over HZSM-5 Zeolite Catalyst Composite

| Time on Stream (hours) | 1 | 2 | 3 | 4 |
|---|---|---|---|---|
| Temperature (°C.) | 250 | 250 | 300 | 300 |
| Conversion of Phenol (wt. %) | 19.66 | 17.18 | 19.61 | 20.80 |
| Selectivity (Area %) | | | | |
| o - IPP | 28.49 | 33.35 | 3.03 | 1.74 |
| m - IPP | 11.90 | 9.31 | 27.45 | 28.48 |
| p - IPP | 47.65 | 46.64 | 31.44 | 35.72 |
| N—Propylphenols | 2.59 | | 36.47 | 33.44 |
| Methyl & Ethyl Phenols | 0 | 10.71 | 1.58 | 0.60 |
| Others* | 9.36 | | 0 | 0 |
| In IPP Fraction | | | | |
| % Ortho | 32.36 | 37.35 | 4.89 | 2.64 |
| % Meta | 13.52 | 10.43 | 44.34 | 43.19 |
| % Para | 54.13 | 52.22 | 50.77 | 54.17 |
| Total Selectivity to IPPs | 88.04 | 89.30 | 61.92 | 65.94 |

*Other products contain mostly $C_9+$ phenolic compounds.

The TABLE II data demonstrate that the ZSM-5 zeolite catalyst, within the temperature range of the present invention, promotes alkylation of phenol which is significantly selective to iso-propylphenols in general and to the para-isopropylphenol isomer in particular. At comparable reaction temperatures, such alkylation produces less of the non-isopropylphenol reaction products than does alkylation over amorphous aluminosilicate as shown in TABLE I.

EXAMPLE III

The HZSM-5 zeolite composition employed as the alkylation catalyst in EXAMPLE II was thereafter regenerated by again calcining it in air at 500° C. for sixteen hours. Alkylation testing using the same phenol/isopropanol mixture was then carried out in the manner and under conditions essentially identical to those described in EXAMPLES I and II.

Results are set forth in TABLE III.

TABLE III

Alkylation of Phenol with Isopropanol to Produce Isopropylphenol (IPP) Over Regenerated HZSM-5 Zeolite Catalyst Composite

| Time on Stream (hours) | 1 | 2 | 3 | 4 | 7 | 8 |
|---|---|---|---|---|---|---|
| Temperature (°C.) | 250 | 300 | 350 | 300 | 300 | 300 |
| Conv. of Phenol (wt. %) | 13.2 | 27.2 | 31.2 | 26.2 | 22.3 | 25.2 |
| Selectivity (Area %) | | | | | | |
| o - IPP | 31.38 | 6.14 | 10.90 | 2.39 | 1.61 | 1.68 |
| m - IPP | 15.06 | 23.68 | 11.92 | 26.06 | 28.77 | 25.58 |
| p - IPP | 42.65 | 17.58 | 6.18 | 29.88 | 36.39 | 35.56 |
| N—Propylphenols | 10.05 | 32.14 | 37.17 | 27.05 | 28.15 | 24.00 |
| Methyl & Ethyl Phenols | 0.31 | 9.45 | 24.19 | 5.68 | 1.79 | 5.64 |
| Others* | 0.55 | 11.01 | 9.64 | 8.94 | 3.27 | 7.56 |
| In IPP Fraction | | | | | | |
| % Ortho | 35.22 | 12.96 | 37.59 | 4.09 | 2.41 | 2.68 |
| % Meta | 16.91 | 49.95 | 41.11 | 44.67 | 43.09 | 40.71 |
| % Para | 47.87 | 37.09 | 21.30 | 51.23 | 54.50 | 56.61 |
| Total Selectivity to IPPs | 89.09 | 47.40 | 29.0 | 58.33 | 66.77 | 62.82 |

*Other products contain mostly $C_9+$ phenolic compounds.

The TABLE III data demonstrate that the regenerated HZSM-5 zeolite catalyst composite, within the temperature range of the present invention, promotes alkylation of phenol which is again significantly selective to isopropylphenols and to para-isopropylphenol isomer. These data further indicate that at the 300° C. alkylation temperature, para-selectivity of the reaction improved with longer times on stream.

EXAMPLE IV

The same phenol-isopropanol feed used in EXAMPLES I, II, III was contacted under essentially identical reaction conditions with calcined HSZSM-5 zeolite material containing no alumina binder.

Alkylation results are set forth in TABLE IV.

TABLE IV

Alkylation of Phenol with Isopropanol to Produce Isopropylphenol (IPP) Over HZSM-5 Zeolite Material

| Time on Stream (hours) | 1 | 2 | 3 | 4 | 5 | 6 | 8 | 9 | 10 | 11** |
|---|---|---|---|---|---|---|---|---|---|---|
| Temperature (°C.) | 250 | 275 | 300 | 325 | 350 | 400 | 300 | 300 | 300 | 300 |
| Conv. of Phenol (wt. %) | 37.3 | 30.3 | 27.5 | 28.9 | 23.8 | 24.1 | 27.7 | 29.9 | 13.4 | 28.8 |
| Selectivity (Area %) | | | | | | | | | | |
| o - IPP | 20.36 | 14.81 | 10.91 | 8.11 | 12.15 | 24.69 | 5.40 | 5.39 | 9.26 | 3.96 |
| m - IPP | 11.87 | 20.71 | 29.91 | 26.63 | 14.46 | 5.16 | 33.21 | 26.74 | 24.49 | 17.09 |
| p - IPP | 63.11 | 55.84 | 38.92 | 35.84 | 6.18 | 7.03 | 38.89 | 53.75 | 65.61 | 75.46 |
| N—Propylphenols | 4.12 | 8.38 | 18.18 | 21.98 | 43.12 | 12.62 | 20.86 | 11.80 | 0 | 3.16 |
| Methyl & Ethyl Phenols | 0.18 | 0.25 | 1.02 | 3.12 | 24.06 | 52.39 | 1.63 | 0 | 0 | 0 |
| Others* | 0 | 0 | 0.31 | 4.31 | 0 | 0 | 0 | 0 | 0 | 0 |
| Tot. Selec. to IPPs | 95.34 | 91.36 | 79.74 | 70.58 | 32.73 | 31.88 | 77.50 | 85.88 | 99.36 | 96.51 |
| In IPP Fraction | | | | | | | | | | |
| % Ortho | 21.35 | 16.22 | 13.68 | 11.49 | 37.05 | 77.45 | 6.96 | 6.28 | 9.34 | 4.10 |
| % Meta | 12.44 | 22.67 | 37.51 | 37.73 | 44.10 | 16.19 | 42.86 | 31.14 | 24.65 | 17.71 |
| % Para | 66.21 | 61.11 | 48.81 | 50.78 | 18.85 | 6.37 | 50.18 | 62.59 | 66.03 | 78.19 |

*Other products contain mostly $C_9+$ phenolic compounds.
**WHSV of 4 for total liquid feed.

The TABLE IV data indicate that high selectivity for production of the para-isopropylphenol isomer can be realized using HZSM-5 zeolite with no binder as a catalyst for alkylation of phenol with isopropanol within the temperature range of the present invention. Furthermore, selectivity toward para-isopropylphenol and total formation of isopropylphenols are increased at longer reaction times at 300° C.

EXAMPLE V

The HZSM-5 zeolite material of EXAMPLE IV (no binder) was regenerated by calcining in air at 500° C. for sixteen hours. Thereafter, a 1:1 molar ratio mixture of phenol and water along with propylene gas were fed into an alkylation reactor. The molar ratio of phenol to propylene was 1, and a WHSV of 1 of liquid was employed.

Alkylation conditions and results are set forth in TABLE V.

TABLE V

Alkylation of Phenols with Propylene to Produce Isopropylphenol (IPP) Over Calcined HZSM-5 Zeolite Material

| Time on Stream (hours) | 1 | 2 | 3 | 4 | 5 | 6 |
|---|---|---|---|---|---|---|
| Temperature (°C.) | 250 | 275 | 300 | 350 | 400 | 300 |
| Conversion (wt. %) | 21.59 | 36.53 | 31.85 | 27.29 | 29.32 | 32.06 |
| Selectivity (Area %) | | | | | | |
| o - IPP | 16.92 | 7.82 | 4.29 | 5.90 | 18.24 | 2.88 |
| m - IPP | 13.67 | 9.01 | 19.42 | 14.49 | 6.87 | 19.25 |
| p - IPP | 64.23 | 77.98 | 54.10 | 10.04 | 3.18 | 61.52 |
| N—Propylphenols | 2.83 | 5.18 | 16.11 | 42.83 | 28.94 | 13.70 |
| Methyl & Ethyl Phenols | 0 | 0 | 3.59 | 13.33 | 32.99 | .98 |
| Others* | 2.32 | 0 | 2.48 | 13.41 | 9.79 | 1.69 |
| Tot. Selec. to IPPs | 94.82 | 94.81 | 77.81 | 30.43 | 28.29 | 83.65 |
| % - IPP | | | | | | |
| o - IPP | 17.84 | 8.25 | 5.52 | 19.40 | 64.46 | 3.44 |
| m - IPP | 14.42 | 9.50 | 24.96 | 47.60 | 24.29 | 23.01 |
| p - IPP | 67.74 | 82.25 | 67.52 | 33.00 | 11.25 | 73.55 |

*Other products contain mostly $C_{9+}$ phenolic compounds.

The TABLE V data indicate that phenol alkylation with propylene over HZSM-5 zeolite material is significantly selective to the para- isopropyl phenol isomer within the temperature range of the present invention. Such alkylation also provides desirably high total formation of isopropylphenols vis-a-vis other possible reaction products.

What is claimed is:

1. A process for selectively alkylating phenol to provide a high yield of an isopropylphenol product enriched in the para-isopropyl isomer of isopropylphenol, said process comprising contacting phenol with a propylating agent selected from propylene and isopropanol in the presence of a zeolite catalyst selected from the group consisting of ZSM-5, ZSM-11, ZSM-23, ZSM-35, ZSM-38 and ZSM-48, under alkylation conditions which include a temperature within the range of from about 200° C. to 300° C.

2. A process for selectively alkylating phenol to provide a high yield of an isopropylphenol product enriched in the para-isopropyl isomer of isopropylphenol, said process comprising contacting phenol with a propylating agent selected from propylene and isopropanol in the presence of a zeolite catalyst which is ZSM-5, under alkylation conditions which include a temperature within the range of from about 200° C. to 300° C.

3. A process according to claim 2 wherein the alkylation conditions further include pressure of from about $10^5$ to $6 \times 10^6$ N/m$^2$ and a weight hourly space velocity of from about 0.5 to 100.

4. A process according to claim 3 wherein the molar ratio of phenol to alkylating agent ranges from about 0.5:1 to 20:1.

5. A process according to claim 4 wherein phenol and alkylating agent are contacted with catalyst in the presence of an inert diluent comprising up to about 50% by weight of the reaction mixture.

6. A process according to claim 4 wherein the zeolite is combined with a binder therefor.

7. A process for selectively alkylating phenol to provide a high yield of an isopropylphenol product enriched in the para-isopropyl isomer of isopropylphenol, said process comprising contacting phenol with a propylating agent selected from propylene and isopropanol in the presence of a ZSM-5 zeolite catalyst, under alkylation conditions which include a temperature of from about 250° C. to 300° C., a pressure of from about $10^5$ to $6 \times 10^6$ N/m$^2$, a weight hourly space velocity of reactants of from about 0.5 to 100 and a molar ratio of phenol to alkylating agent of from about 0.5:1 to 20:1.

8. A process according to claim 1, 2, 3, 4, 5, 6 or 7 wherein the alkylating agent is isopropanol.

9. A process according to claim, 1, 2, 3, 4, 5, 6 or 7 wherein the alkylating agent is propylene.

* * * * *